United States Patent [19]

Meyer et al.

[11] Patent Number: 4,741,760
[45] Date of Patent: May 3, 1988

[54] PYRIMIDINE DERIVATIVES HAVING A HERBICIDAL ACTION AND AN ACTION REGULATING PLANT GROWTH

[75] Inventors: Willy Meyer, Riehen; Karl Hoegerle, Basel; Rudolph C. Thummel, Courgenay; Hans Tobler, Allschwil; Beat Böhner, Binningen, all of Switzerland

[73] Assignee: Ciba-Geigy Corporation, Ardsley, N.Y.

[21] Appl. No.: 938,674

[22] Filed: Dec. 5, 1986

Related U.S. Application Data

[63] Continuation of Ser. No. 780,547, Sep. 26, 1985, abandoned, which is a continuation of Ser. No. 610,223, May 14, 1984, abandoned.

[30] Foreign Application Priority Data

May 16, 1983 [CH] Switzerland .......... 2636/83

[51] Int. Cl.$^4$ .................. C07D 239/69; A01N 43/54
[52] U.S. Cl. .......................................... 71/92; 71/90; 544/317; 544/321; 544/323; 544/324; 544/327; 544/331; 544/332
[58] Field of Search ............. 71/90, 92; 544/317, 544/319, 320, 321, 323, 324, 327, 331, 332

[56] References Cited

U.S. PATENT DOCUMENTS

| | | | |
|---|---|---|---|
| 4,221,585 | 9/1980 | Levitt | 71/92 |
| 4,310,346 | 1/1982 | Levitt et al. | 71/92 |
| 4,383,113 | 5/1983 | Levitt | 71/93 |
| 4,394,506 | 7/1983 | Levitt | 544/321 |
| 4,398,939 | 8/1983 | Levitt | 71/90 |
| 4,435,205 | 3/1984 | Reap | 71/92 |
| 4,435,206 | 3/1984 | Levitt | 71/92 |
| 4,441,910 | 4/1984 | Shapiro | 71/90 |

Primary Examiner—John M. Ford
Attorney, Agent, or Firm—Edward McC. Roberts; Kevin T. Mansfield

[57] ABSTRACT

N-Pyrimidin-4-yl-N'-sulfonylureas of the formula I and the basic addition salts thereof have herbicidal properties and properties for regulating, especially inhibiting, plant growth:

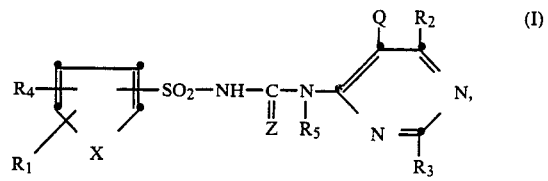

the symbols in this formula having the following meanings:

Q is halogen, lower alkyl, lower haloalkyl, lower alkoxy, lower haloalkoxy, nitro, amino, lower alkyl or dialkylamino, lower alkoxycarbonyl, formyl, lower alkoxyalkyl, lower alkoxyalkoxy, lower alkylthio, lower alkylsulfinyl or alkylsulfonyl, $C_1$–$C_4$-alkenyl or $C_1$–$C_4$-alkynyl, $R_1$ is hydrogen, halogen, nitro, a ketal radical, a carbonyl radical substituted by allyl, haloalkyl, alkoxy or cycloalkyl, or is an oxime radical, a lower alkoxy, lower alkylthio, lower alkyl, lower alkylsulfinyl or sulfonyl group, $R_2$ and $R_3$ independently of one another are each hydrogen, halogen, lower alkyl, lower haloalkyl, lower alkoxy, lower haloalkoxy, lower alkylthio, lower alkoxyalkyl, lower alkoxyalkoxy, amino, lower alkyl- or dialkylamino or cyclopropyl, and $R_2$ and Q together can also form a 2-4-membered carbon chain, which is optionally interrupted by an oxygen or sulfur atom or by the group —$NR_5$—, $R_4$ is hydrogen, halogen, lower alkyl, methoxy, nitro or trifluoromethyl, $R_5$ is hydrogen, $C_1$–$C_4$-alkyl or $C_3$–$C_4$-alkenyl, X is oxygen, sulfur, —$NR_5$—,

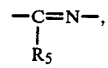

—CH=CH— or an annularly-linked phenyl ring, and Z is oxygen or sulfur.

8 Claims, No Drawings

PYRIMIDINE DERIVATIVES HAVING A HERBICIDAL ACTION AND AN ACTION REGULATING PLANT GROWTH

This is a continuation of application Ser. No. 780,547 filed on Sept. 26, 1985, abandoned, which is a continuation of application Ser. No. 610,223, filed on May 14, 1984, abandoned.

The present invention relates to novel N-pyrimidin-4-yl-N'-sulfonylureas having a herbicidal action and an action regulating plant growth, to processes for producing them, to compositions containing them as active ingredients, and to the use thereof for controlling weeds, particularly in crops of useful plants, or for regulating and reducing plant growth.

The N-pyrimidin-4-yl-N'-sulfonylureas according to the invention correspond to the formula I

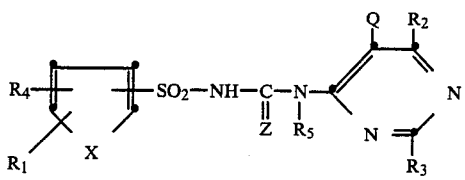

wherein

Q is halogen, $C_1$-$C_4$-alkyl, $C_1$-$C_4$-haloalkyl, $C_1$-$C_4$-alkoxy, $C_1$-$C_4$-haloalkoxy, nitro, amino, $C_1$-$C_4$-alkylamino, $C_1$-$C_4$-dialkylamino, cyano, $C_1$-$C_4$-alkoxycarbonyl, formyl, $C_2$-$C_4$-alkoxyalkyl, $C_1$-$C_4$-alkylthio, C-$C_4$-alkylsulfinyl, $C_1$-$C_4$-alkylsulfonyl, $C_1$-$C_4$-alkenyl or $C_1$-$C_4$-alkynyl, $R_1$ is hydrogen, halogen, nitro or a radical

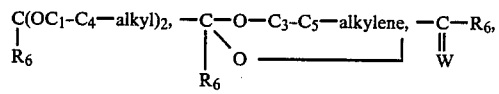

—$SO_2NR_7R_8$, —$COR_9$ or —$(Y)_m$—$R_{10}$, $R_2$ and $R_3$ independently of one another are each hydrogen, halogen, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylthio, $C_2$-$C_4$-alkoxyalkyl, $C_2$-$C_4$-alkoxyalkoxy, amino, $C_1$-$C_4$-alkylamino, $C_1$-$C_4$-dialkylamino or cyclopropyl, and Q and $R_2$ together can also form a 2-4-membered carbon chain, which is optionally interrupted by an oxygen or sulfur atom or by the group N—$R_5$, $R_4$ is hydrogen, halogen, $C_1$-$C_4$-alkyl, methoxy, nitro or trifluoromethyl, $R_5$ is hydrogen, $C_1$-$C_4$-alkyl or $C_3$-$C_4$-alkenyl, X is oxygen, sulfur, —$NR_5$—,

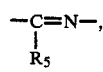

—CH=CH— or an annularly-linked phenyl ring,

Z is oxygen or sulfur, $R_6$ is hydrogen, $C_1$-$C_4$-alkyl, $C_1$-$C_4$-haloalkyl, $C_3$-$C_6$-cycloalkyl, $C_4$-$C_7$-cycloalkylalkyl or $C_2$-$C_4$-alkoxyalkyl, $R_7$ is hydrogen, $C_1$-$C_4$-alkyl, $C_1$-$C_4$-cyanoalkyl, methoxy or ethoxy, $R_8$ is the same as $R_5$, or $R_7$ and $R_8$ together with the nitrogen atom linking them form a 5- or 6-membered saturated heterocycle optionally containing an oxygen or sulfur atom as ring member, $R_9$ is $C_1$-$C_4$-alkoxy, $C_3$-$C_6$-alkenyloxy, $C_3$-$C_6$-alkynyloxy, $C_2$-$C_6$-haloalkoxy, $C_1$-$C_4$-cyanoalkoxy, $C_1$-$C_4$-alkylthio, $C_3$-$C_4$-alkenylthio, $C_3$-$C_4$-alkynylthio, $C_5$-$C_6$-cycloalkoxy, $C_4$-$C_7$-cycloalkylalkoxy, —$NR_7R_8$ or $C_2$-$C_6$-alkoxyalkoxy, $R_{10}$ is $C_1$-$C_4$-alkyl, unsubstituted or mono- or polysubstituted by halogen, cyano, methoxy, ethoxy, nitro, $C_1$-$C_2$-alkyl-S(O)$_n$, $C_1$-$C_2$-haloalkoxy, $C_1$-$C_2$-haloalkylthio, —$COR_6$, —$COR_9$ or —$SO_2NR_7R_8$, or is $C_2$-$C_4$-alkenyl, unsubstituted or mono- or polysubstituted by halogen, nitro, cyano, methoxy, ethoxy or $C_1$-$C_2$-alkyl-(S)O$_n$, or is $C_2$-$C_4$-alkynyl, m is zero or 1, n is zero, 1 or 2, W is oxygen or the group =N—O—$R_5$, and Y is oxygen, sulfur, —SO— or —$SO_2$—, with the proviso that in the radical $R_1$ in the group —$(Y)_m$—$R_{10}$, $R_{10}$ is only $C_3$-$C_4$-alkynyl when m is 1.

The invention embraces also the salts of these sulfonylureas.

N-Pyrimidin-4-yl-N'-sulfonylureas unsubstituted in the 5-position of the pyrimidine ring and having herbicidal activity are known, for example from the European Offenlegungsschriften Nos. EP-A 1485, 13 480 and 44 212.

N-Pyrimidin-2-yl-N'-sulfonylureas substituted in the 5-position and having a herbicidal action are known from the U.S. Pat. No. 4,342,587.

And N-pyrimidin-4-yl-N-alkylsulfonylureas substituted in the 5-position and having herbicidal activity are moreover described in European Patent Application No. EP-A No. 61 661.

The present N-pyrimidin-4-yl-sulfonylureas which are substituted in the 5-position of the pyrimidine ring by a radical Q are novel. They are distinguished by an excellent herbicidal, selective-herbicidal and plant-growth-regulating action, the desired effect being obtained with applied amounts of less than 1 kg per hectare.

In the definitions of $R_1$ to $R_{11}$, an alkyl group is straight-chain or branched-chain, for example: methyl, ethyl, n-propyl, i-propyl, the four isomeric butyl groups, n-amyl, i-amyl, 2-amyl or 3-amyl; the alkyl group is preferably however straight-chain.

By alkoxy in the definitions is meant: methoxy, ethoxy, n-propyloxy, i-propyloxy and the four isomeric butyloxy groups, especially however methoxy or ethoxy.

Examples of alkylthio are methylthio, ethylthio, n-propylthio, i-propylthio and n-butylthio, particularly methylthio and ethylthio.

Examples of alkenyl groups are: vinyl, allyl, isopropenyl, 1-propenyl, 1-butenyl, 2-butenyl, 3-butenyl, 1-isobutenyl, 2-isobutenyl, 1-pentenyl, 2-pentenyl, 3-pentenyl and 4-pentenyl, in particular however vinyl, allyl and 4-pentenyl.

Alkynyl groups are for example: ethinyl, propargyl, 1-propynyl, the three isomeric butynyl groups as well as 4-pentynyl, but preferably the propargyl group.

By halogen is meant in the above definitions and also in haloalkyl: fluorine, chlorine, bromine and iodine, preferably however fluorine and in particular chlorine.

In the definitions, cycloalkyl is for example: cyclopropyl, cyclobutyl, cyclopentyl or cyclohexyl, preferably cyclopropyl, cyclopentyl or cyclohexyl.

The invention embraces likewise the salts which the compounds of the formula I can form with amines, alkali metal bases and alkaline-earth metal bases or quaternary ammonium bases.

Alkali metal hydroxides and alkaline-earth metal hydroxides to be emphasised as salt formers are hydroxides of lithium, sodium, potassium, magnesium or calcium, especially those of sodium and potassium.

Examples of amines suitable for salt formation are: primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline, and i-quinoline, particularly ethyl-, propyl-, diethyl- or triethylamine, especially isopropylamine and diethanolamine.

Examples of quaternary ammonium bases are in general the cations of haloammonium salts, for example: the tetramethylammonium cation, the trimethylbenzylammonium cation, the triethylbenzylammonium cation, the tetraethylammonium cation or the trimethylethylammonium cation, and also the ammonium cation.

The best effects have been obtained with the compounds corresponding to the following formula:

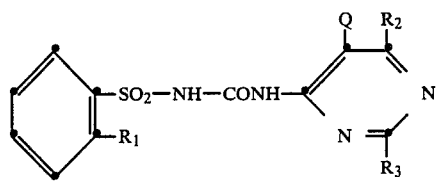
(Ia)

wherein Q, $R_1$ and $R_2$ have the meanings defined in the foregoing, whilst $R_3$ is $C_1$-$C_2$-alkyl, $C_1$-$C_2$-haloalkyl, cyclopropyl, $C_1$-$C_3$-alkoxy, $C_1$-$C_2$-haloalkoxy, methylthio or difluoromethylthio.

Compounds of the formula Ia which have proved to be particularly effective are those in which
Q is halogen, $C_1$-$C_4$-alkyl, nitro, amino, formyl, methylthio, methylsulfinyl or methylsulfonyl,
$R_1$ is halogen, nitro, $C_1$-$C_4$-haloalkyl, $C_1$-$C_4$-alkoxy, $C_1$-$C_4$-haloalkoxy, $C_3$-$C_4$-alkenyloxy, $C_2$-$C_4$-haloalkenyloxy, $C_1$-$C_4$-haloalkylthio, $C_1$-$C_4$-alkoxycarbonyl, $C_1$-$C_4$-alkylsulfonyl or dimethylsulfamoyl,
$R_2$ is halogen, $C_1$-$C_3$-alkyl, cyclopropyl, $C_1$-$C_3$-alkoxy, $C_1$-$C_2$-haloalkoxy, amino, methylamino, dimethylamino or difluoromethylthio, and
$R_3$ is $C_1$-$C_2$-alkyl, $C_1$-$C_2$-haloalkyl, cyclopropyl, $C_1$-$C_3$-alkoxy, $C_1$-$C_2$-haloalkoxy, methylthio or difluoromethoxy;
particularly however those compounds in which Q has the above meaning, and
$R_1$ is halogen, nitro, $C_1$-$C_4$-haloalkyl, $C_1$-$C_4$-haloalkoxy, $C_1$-$C_4$-haloalkylthio, $C_1$-$C_4$-alkoxycarbonyl or dimethylsulfamoyl,
$R_2$ is halogen, $C_1$-$C_2$-alkyl, $C_1$-$C_2$-alkoxy, $C_1$-$C_2$-haloalkoxy, methylamino or dimethylamino, and
$R_3$ is $C_1$-$C_2$-alkoxy, trifluoroethoxy or difluoromethoxy.

The following individual compounds are distinguished by virtue of their good action:

N-(2-methoxycarbonylphenylsulfonyl)-N'-(2,6-dimethoxy-5-methylpyrimidin-4-yl) urea; and
N-(2-difluoromethoxyphenylsulfonyl)-N'-(2,6-dimethoxy-5-methylpyrimidin-4-yl) urea.

The compounds of the formula I are produced, in a manner known per se, in an inert organic solvent.

According to one process, the compounds of the formula I are produced by reacting a sulfonamide of the formula I are produced by reacting a sulfonamide of the formula II

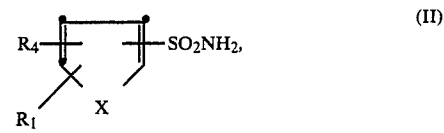
(II)

wherein $R_1$, $R_4$ and X have the same meanings defined in the foregoing, in the presence of a base, with a pyrimidin-4-yl-carbamate of the formula III

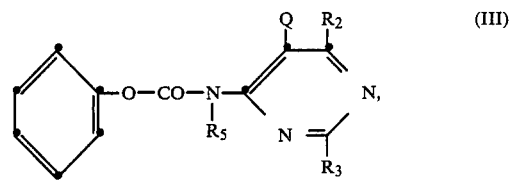
(III)

wherein Q, $R_2$, $R_3$ and $R_5$ have the meanings defined under the formula I; and optionally converting the product obtained into a salt.

According to a second process, compounds of the formula I are obtained by reacting a phenylsulfonylisocyanate of the formula IV

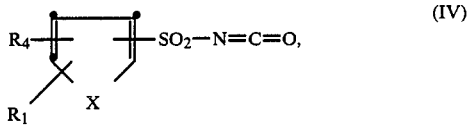
(IV)

wherein $R_1$, $R_4$ and X have the meanings defined in the foregoing, optionally in the presence of a base, with an amine of the formula V

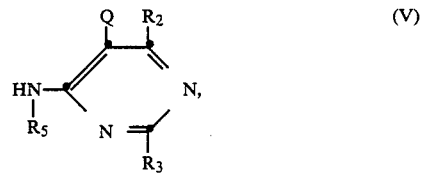
(V)

wherein Q, $R_2$, $R_3$ and $R_5$ have the meanings given above; and optionally converting the product obtained into a salt.

According to a further process, the compounds of the formula I in which $R_5$ is hydrogen are produced by reacting a sulfonamide of the above-given formula II, optionally in the presence of a base, with an isocyanate of the formula VI

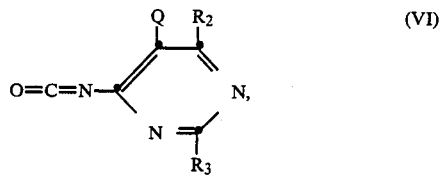

wherein Q, $R_2$ and $R_3$ have the meanings defined in the foregoing; and optionally converting the product obtained into a salt.

Finally, the compounds of the formula I can be obtained also by reacting an N-phenylsulfonylcarbamate of the formula VII

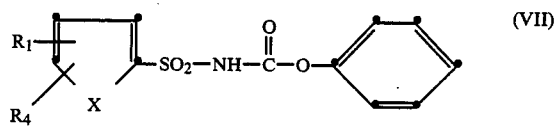

wherein $R_1$, $R_4$ and X have the meanings defined in the foregoing, with an amine of the formula V given above; and optionally converting the product obtained into a salt.

The resulting ureas of the formula I can if required be converted, by means of amines, alkali metal hydroxides or alkaline-earth metal hydroxides or quaternary ammonium bases, into basic addition salts. This is effected for example by reaction with the equimolar amount of a base, and removal of the solvent by evaporation. Such reactions are known, and are described for example in the U.S. Pat. Nos. 2,384,757 and 3,410,887.

The starting materials of the formulae II to VII are in part known, and can be produced by generally known methods.

Thus, the sulfonamides of the formula II can be obtained from the corresponding amines by diazotisation and exchange of the diazo group for sulfur dioxide in the presence of a catalyst, such as copper(II) chloride, in acetic acid, in the process of which the sulfonyl chloride is formed (cp. J. Org. Chem. 25, 1824 (1960)); and subsequent reaction of the formed sulfonyl chloride with an ammonium hydroxide solution.

The sulfonylisocyanates of the formula IV can be obtained by reaction of the sulfonamides of the formula II with phosgene in the presence of butylisocyanate, in a chlorinated hydrocarbon as solvent, at the refluxing temperature (cp. in this respect "Newer Methods of Preparative Organic Chemistry", Vol. VI, 223-241, Academic Press, New York and London).

Amines of the formula V are known and some are obtainable commercially, or they can be produced by known methods (cp. "The Chemistry of Heterocyclic Compounds", Viol. XVI+Suppl. I, Interscience Publishers, New York and London).

The isocyanates of the formula VI can be produced by reaction of amines of the formula V with phosgene or oxalyl chloride in a chlorinated hydrocarbon as solvent.

The sulfonylcarbamates of the formula VII are obtained by reaction of the sulfonamide of the formula II with diphenylcarbamate in the presence of a base (cp. Japanese Patent Specification No. 61 169).

The carbamates of the formula III are obtained from the amines of the formula V in an analogous manner.

These reactions are advantageously performed in aprotic, inert organic solvents, such as methylene chloride, tetrahydrofuran, acetonitrile, dioxane or toluene.

The reaction temperatures are preferably between $-20°$ and $+120°$ C. The reactions proceed in general slightly exothermically and can be performed at room temperature. For the purpose of shortening the reaction time or of initiating the reaction, heat is advantageously applied for a short time up to the boiling point of the reaction mixture. The reaction times can be if required shortened by the addition of a few drops of a base or isocyanate as a reaction catalyst.

The final products can be isolated by concentration by evaporation and/or by evaporating off the solvent, and purified by recrystallisation or trituration of the solid residue in solvents in which the products do not readily dissolve, such as ethers, aromatic hydrocarbons or chlorinated hydrocarbons.

The active substances of the formula I are stable compounds, and the handling of them requires no special precautions.

The compounds of the formula I are distinguished by good selective-herbicidal properties, which render them excellently suitable for use in crops of cultivated plants, for example in crops of wheat, maize and soyabean. It is possible to some cases also to destroy weeds which could be dealt with hitherto only by the application of total herbicides.

The mode of action of these herbicides is unusual: they are capable of being translocated, that is to say, they are taken up by the plant and transported to other locations, where they produce the desired effect. The unusual feature is not only that they take the path of the nutrients through the vascular bundle in the xylem from the roots into the leaves, but also that they can be translocated through the sieve tubes in the bast part from the leaves back into the roots. It is thus possible for example by surface treatment of perennial weeds to destroy them at the roots. The novel compounds of the formula I are effective in applied amounts which are very small compared with the amounts required to obtain the same effect using other herbicides.

The compounds of the formula I also have excellent properties for regulating plant growth, the effects of which can mean an increase in the yield of cultivated plants or of harvested crops. Many compounds of the formula I exhibit moreover an action reducing plant growth to an extent depending on the concentration used. Both monocotyledons and dicotyledons are impaired in their growth.

Thus, for example, the leguminosae frequently planted as cover crops in agriculture in tropical regions can be selectively inhibited in their growth by the compounds of the formula I, the result being that soil erosion between the cultivated plants is prevented, without the cover crops being able to compete with the main cultivated crop.

A reduction of the vegetative growth enables in the case of many cultivated plants the crop density to be increased, so that higher yields for the same area of land can be achieved.

An additional factor contributing to the increase in yield with the use of growth inhibitors is that the formation of blossom and fruit benefits to a greater extent from the nutritive substances, because the vegetative growth is restricted.

In the case of monocotyledonous plants, for example grasses, or cultivated plants such as cereals, a reduction of vegetative growth is sometimes desirable and advantageous. A reduction of growth of this kind is of economic interest with regard to, amongst other things, grasses, for as a consequence it is possible to reduce the frequency of the cutting of grass in ornamental gardens, parks and sports grounds, or along the verges of highways. Of importance also is the inhibition of the growth of herbaceous and ligneous plants at the edges of roads and in the vicinity of overhead transmission lines, or quite generally in areas where a strong growth is undesirable.

Also important is the application of growth regulators for reducing the growth in height of cereals, since a shortening of the stems lessens or completely removes the danger of the snapping off (flattening) of the plants before harvesting. Furthermore, growth regulators can result in a strengthening of the stems of cereal crops, a further factor acting to prevent bending of the stems of the plants.

The compounds of the formula I are likewise suitable for preventing the sprouting of stored potatoes. Shoots frequently form on potatoes being stored during the winter, and these shoots cause shrinkage, loss in weight and rotting.

With larger applied amounts of active substance, all the tested plants are impaired in their development to the extent that they wither.

The present invention relates also to herbicidal and plant-growth-regulating compositions containing a novel active ingredient of the formula I, and also to processes for the pre- and post-emergence controlling of weeds, and for the reduction of growth of monocotyledonous and dicotyledonous plants, particularly that of grasses, tropical cover crops and side shoots of tobacco plants.

The compounds of the formula I are used either in an unmodified form or preferably in compositions, together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of compositions, are selected to suit the objects to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salts of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanol, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22C atoms and, as further substituents, lower, optionally halogenated alkyl, benzyl or lower hydroxyalkyl groups. The salts are preferably in the form of halides, methyl sulfates or ethyl sulfates, for example stearyl-trimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual", MC Publishing Corp., Ridgewood, N.J., 1979;

M. and J. Ash, "Encyclopedia of Surfactants", Vol. I-III, Chemical Publishing Co., Inc. New York 1980–1981;

H. Stache, "Tensid Taschenbuch", 2nd Edition, C. Hanser Verlag, Munich and Vienna, 1981.

The agrochemical preparations contain as a rule 0.1 to 95%, especially 0.1 to 80%, of active ingredient of the formula I, 1 to 99.9% of a solid or liquid additive, and 0 to 25%, particularly 0.1 to 25% of a tenside.

Preferred formulations are made up in particular as follows (%=percent by weight):

Emulsifiable concentrates active ingredient: 1 to 20%, preferably 5 to 10%
surface active agent: 5 to 30%, preferably 10 to 20%
liquid carrier: 50 to 94%, preferably 70 to 85%.

Dusts active ingredient: 0.1 to 10%, preferably 0.1 to 1%
solid carrier: 99.9 to 90%, preferably 99.9 to 99%.

Suspension concentrates active ingredient: 5 to 75%, preferably 10 to 50%
water: 94 to 25%, preferably 90 to 30%
surface-active agent: 1 to 40%, preferably 2 to 30%.

Wettable powders active ingredient: 0.5 to 90%, preferably 1 to 80%
surface-active agent: 0.5 to 20%, preferably 1 to 15%
solid carrier: 5 to 95%, preferably 15 to 90%.

Granulates active ingredient: 0.5 to 30%, preferably 3 to 15%
solid carrier: 99.5 to 70%, preferably 97 to 85%.

Whereas commercial products are preferably in the form of concentrated compositions, the compositions employed by the end-user are as a rule diluted. The preparations can for application be diluted down to 0.001% of active ingredient. The applied amounts are usually 0.001 to 10 kg, preferably 0.025 to 5 kg, of active substance per hectare.

The compositions can also contain additives such as stabilisers, antifoaming agents, viscosity regulators, binders and adhesives, as well as fertilisers or other active substances for obtaining special effects.

In the following Examples, parts and percentages relate to weight, and pressure values are given in millibars (mb) (1 mb=100 Pascal).

EXAMPLE 1

Production of N-(2-methoxycarbonylphenylsulfonyl)-N'-(2,6-dimethoxy-5-methyl-pyrimidin-4-yl)-urea

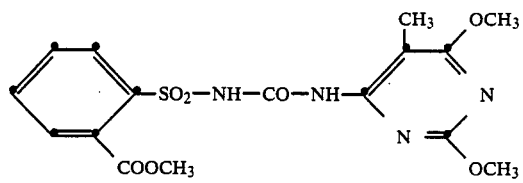

2.41 g of 2-methoxycarbonylphenylsulfonylisocyanate and 1.7 g of 4-amino-2,6-dimethoxy-5-methylpyrimidine are stirred up with 40 ml of absolute dioxane at 80°–85° C. for 2 hours; and the formed suspension is subsequently fully concentrated by evaporation. From the residue are then obtained, by recrystallisation from a mixture of acetone and ether, 3.4 g of N-(2-carboxymethylphenylsulfonyl)-N'-(2,6-dimethoxy-5-methyl-pyrimidin-4-yl)-urea, m.p. 195°–196° C.

The 4-amino-2,6-dimethoxy-5-methylpyrimidine required as intermediate is obtained as follows.

(a) Production of 5-methylbarbituric acid 46 g (2 mols) of sodium are dissolved in 1 liter of absolute ethanol in a 5-liter flask. To this solution are firstly added 348 g (2 mols) of methyl malonic acid methyl ester; and there is then added dropwise at 70° C. with stirring, within about 5 minutes, a solution of 120 g (2 mols) of urea in 1 liter of absolute ethanol. There is formed a thin suspension, which is diluted with 3.5 liters of ethanol, refluxed for 16 hours and afterwards cooled. There are subsequently added 2 liters of water and, for clearing, a filtering auxiliary (HiFlo) is introduced, and the suspension is filtered. Concentrated hydrochloric acid is then added until a Congo blue colour is indicated, and the mixture is left to stand for several hours in a cool place. A fine white crystalline precipitate is formed, which is filtered and dried. The mother liquor is concentrated by evaporation, diluted with water, and the precipitate is likewise filtered and dried. The crude yield is 263 g of material, which melts at 200°–215° C. After recrystallisation from water, there remain 144 g of white crystals (58% of theory), which melt at 203°–204° C.

(b) Production of 5-methyl-2,4,6-trichloropyrimidine 450 ml (2.94 mols) of phosphorus oxychloride are placed into a 2-liter flask, and 49.3 ml (0.39 mol) of commercial N,N-dimethylaniline are slowly added with cooling and stirring. There are then added portionwise, within 20 minutes, 142 g (1 mol) of methylbarbituric acid, which produces an exothermic reaction. The reaction mixture is allowed to heat up, and is finally refluxed for 5 hours until the evolution of gas has ceased. The suspension is subsequently slowly poured into water, care being taken that the temperature remains at 25°–30° C. The aqueous suspension is filtered with suction, and the filter residue is dissolved in 250 ml of dichloromethane; the solution is filtered until clear, and extracted twice with 250 ml of ice-water each time. The organic phase is then dried, concentrated by evaporation, and the residue occurring in crystalline form is dried in vacuo. The yield is 126.7 g of crystalline 5- methyl-2,4,6-trichloropyrimidine, which melts at 67°–68° C. (yield=64.2% of theory).

(c) Production of 4-amino-2,6-dichloro-5-methylpyrimidine 39.5 g (0.2 mol) of 5-methyl-2,4,6-trichloropyrimidine are dissolved in 250 ml of dimethoxyethane, and ammonia gas is then introduced at room temperature until the solution is saturated. A white suspension is formed, which is stirred for 12 hours at room temperature; it is subsequently concentrated in a rotary evaporator, and 200 ml of water are added to the residue. The formed suspension is filtered and the precipitate is dried. The mother liquor is concentrated to half the volume, filtered, and the precipitate is dried. There are thus obtained 26.4 g of crude product, which is recrystallised from acetonitrile/water (5:1); m.p. 193°–194° C. (yield=75% of theory).

Analysis: calculated: C 33.74%, H 2.83%, N 23.61%, Cl 39.83%, found: C 33.80%, H 2.87%, N 23.44%, Cl 39.51%.

(d) Production of 4-amino-2,6-dimethoxy-5-methylpyrimidine

A mixture of 10.7 g (0.06 mol) of 5-methyl-4-amino-2,6-dichloropyrimidine, 100 ml of methanol and 22 g of 30% sodium methylate (0.122 mol) is allowed to react at 120° C. for 20 hours in an autoclave. After cooling, the grey reaction mixture is concentrated in vacuo; the residue is taken up in 70 ml of water, stirred and then filtered. The residue is washed with water, dried and recrystallised from carbon tetrachloride. There remain after drying 6.1 g of 4-amino-5-methyl-2,6-dimethoxypyrimidine as white crystals, which melt at 60° C. (yield=60% of theory).

Analysis: calculated: C 49.70%, H 6.55%, N 24.84%, O 18.91%, found: C 49.45%, H 6.42%, N 24.59%, O 19.84%.

The following compounds are produced in a manner analogous to this Example:

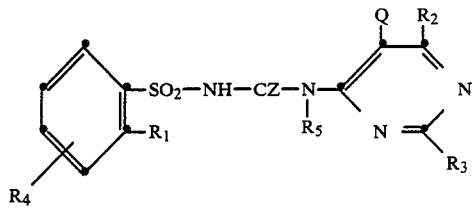

TABLE 1

| No. | Q | $R_1$ | $R_2$ | $R_3$ | $R_4$ | $R_5$ | Z | Phys. data m.p. °C. |
|---|---|---|---|---|---|---|---|---|
| 1.1 | $CH_3$ | $COOCH_3$ | $CH_3$ | $OCH_3$ | H | H | O | |
| 1.2 | $CH_3$ | $COOCH_3$ | $OCH_3$ | $OCH_3$ | H | H | O | 195–196° |
| 1.3 | $CH_3$ | $COOCH_3$ | $C_2H_5$ | $OCH_3$ | H | H | O | |
| 1.4 | $CH_3$ | $COOCH_3$ | $N(CH_3)_2$ | $OCH_3$ | H | H | O | |
| 1.5 | $CH_3$ | $COOCH_3$ | $CH_2F$ | $OCH_3$ | H | H | O | |
| 1.6 | $CH_3$ | $COOCH_3$ | cyclopropyl | $OCH_3$ | H | H | O | |
| 1.7 | $CH_3$ | $COOCH_3$ | $SCH_3$ | $OCH_3$ | H | H | O | |
| 1.8 | $CH_3$ | $COOCH_3$ | $CH_2OCH_3$ | $OCH_3$ | H | H | O | |
| 1.9 | $CH_3$ | $COOCH_3$ | $CH_2OC_2H_5$ | $OCH_3$ | H | H | O | |
| 1.10 | $CH_3$ | $COOCH_3$ | $NHCH_3$ | $OCH_3$ | H | H | O | |
| 1.11 | $CH_3$ | $COOCH_3$ | $NH_2$ | $OCH_3$ | H | H | O | |
| 1.12 | $CH_3$ | $COOCH_3$ | $OCH_2CF_3$ | $OCH_3$ | H | H | O | 158–159° |
| 1.13 | $CH_3$ | $COOCH_3$ | $OCHF_2$ | $OCH_3$ | H | H | O | |
| 1.14 | $CH_3$ | $COOCH_3$ | $OC_2H_4OCH_3$ | $OCH_3$ | H | H | O | |
| 1.15 | $CH_3$ | $COOCH_3$ | Cl | $OCH_3$ | H | H | O | |
| 1.16 | $CH_3$ | $COOCH_3$ | $OC_2H_5$ | $OCH_3$ | H | H | O | |
| 1.17 | Cl | $COOCH_3$ | $CH_3$ | $OCH_3$ | H | H | O | |
| 1.18 | Cl | $COOCH_3$ | $OCH_3$ | $OCH_3$ | H | H | O | 188–189° |
| 1.19 | Cl | $COOCH_3$ | $C_2H_5$ | $OCH_3$ | H | H | O | |
| 1.20 | Cl | $COOCH_3$ | $N(CH_3)_2$ | $OCH_3$ | H | H | O | 192–194° |
| 1.21 | Cl | $COOCH_3$ | $CH_2F$ | $OCH_3$ | H | H | O | |
| 1.22 | Cl | $COOCH_3$ | cyclopropyl | $OCH_3$ | H | H | O | |
| 1.23 | Cl | $COOCH_3$ | $SCH_3$ | $OCH_3$ | H | H | O | |
| 1.24 | Cl | $COOCH_3$ | $CH_2OCH_3$ | $OCH_3$ | H | H | O | |
| 1.25 | Cl | $COOCH_3$ | $CH_2OC_2H_5$ | $OCH_3$ | H | H | O | |
| 1.26 | Cl | $COOCH_3$ | $NHCH_3$ | $OCH_3$ | H | H | O | |
| 1.27 | Cl | $COOCH_3$ | $NH_2$ | $OCH_3$ | H | H | O | |
| 1.28 | Cl | $COOCH_3$ | $OCH_2CF_3$ | $OCH_3$ | H | H | O | |
| 1.29 | Cl | $COOCH_3$ | $OCHF_2$ | $OCH_3$ | H | H | O | |
| 1.30 | Cl | $COOCH_3$ | $OC_2H_4OCH_3$ | $OCH_3$ | H | H | O | |
| 1.31 | Cl | $COOCH_3$ | Cl | $OCH_3$ | H | H | O | 198–200° |
| 1.32 | Cl | $COOCH_3$ | $OC_2H_5$ | $OCH_3$ | H | H | O | |
| 1.33 | $CH_3$ | $OCHF_2$ | $CH_3$ | $OCH_3$ | H | H | O | |
| 1.34 | $CH_3$ | $OCHF_2$ | $OCH_3$ | $OCH_3$ | H | H | O | 184–185° |
| 1.35 | $CH_3$ | $OCHF_2$ | $C_2H_5$ | $OCH_3$ | H | H | O | |
| 1.36 | $CH_3$ | $OCHF_2$ | $N(CH_3)_2$ | $OCH_3$ | H | H | O | |
| 1.37 | $CH_3$ | $OCHF_2$ | $CH_2F$ | $OCH_3$ | H | H | O | |
| 1.38 | $CH_3$ | $OCHF_2$ | cyclopropyl | $OCH_3$ | H | H | O | |
| 1.39 | $CH_3$ | $OCHF_2$ | $SCH_3$ | $OCH_3$ | H | H | O | |
| 1.40 | $CH_3$ | $OCHF_2$ | $CH_2OCH_3$ | $OCH_3$ | H | H | O | |
| 1.41 | $CH_3$ | $OCHF_2$ | $CH_2OC_2H_5$ | $OCH_3$ | H | H | O | |
| 1.42 | $CH_3$ | $OCHF_2$ | $NHCH_3$ | $OCH_3$ | H | H | O | |
| 1.43 | $CH_3$ | $OCHF_2$ | $NH_2$ | $OCH_3$ | H | H | O | |
| 1.44 | $CH_3$ | $OCHF_2$ | $OCH_2CF_3$ | $OCH_3$ | H | H | O | |
| 1.45 | $CH_3$ | $OCHF_2$ | $OCHF_2$ | $OCH_3$ | H | H | O | |
| 1.46 | $CH_3$ | $OCHF_2$ | $OC_2H_4OCH_3$ | $OCH_3$ | H | H | O | |
| 1.47 | $CH_3$ | $OCHF_2$ | Cl | $OCH_3$ | H | H | O | |
| 1.48 | $CH_3$ | $OCHF_2$ | $OC_2H_5$ | $OCH_3$ | H | H | O | |

TABLE 1-continued

| No. | Q | $R_1$ | $R_2$ | $R_3$ | $R_4$ | $R_5$ | Z | Phys. data m.p. °C. |
|---|---|---|---|---|---|---|---|---|
| 1.49 | Cl | $OCHF_2$ | $CH_3$ | $OCH_3$ | H | H | O | 177–178° |
| 1.50 | Cl | $OCHF_2$ | $OCH_3$ | $OCH_3$ | H | H | O | 190–191° |
| 1.51 | Cl | $OCHF_2$ | $C_2H_5$ | $OCH_3$ | H | H | O | |
| 1.52 | Cl | $OCHF_2$ | $N(CH_3)_2$ | $OCH_3$ | H | H | O | 169–170° |
| 1.53 | Cl | $OCHF_2$ | $CH_2F$ | $OCH_3$ | H | H | O | |
| 1.54 | Cl | $OCHF_2$ | cyclopropyl | $OCH_3$ | H | H | O | |
| 1.55 | Cl | $OCHF_2$ | $SCH_3$ | $OCH_3$ | H | H | O | |
| 1.56 | Cl | $OCHF_2$ | $CH_2OCH_3$ | $OCH_3$ | H | H | O | |
| 1.57 | Cl | $OCHF_2$ | $CH_2OC_2H_5$ | $OCH_3$ | H | H | O | |
| 1.58 | Cl | $OCHF_2$ | $NHCH_3$ | $OCH_3$ | H | H | O | |
| 1.59 | Cl | $OCHF_2$ | $NH_2$ | $OCH_3$ | H | H | O | |
| 1.60 | Cl | $OCHF_2$ | $OCH_2CF_3$ | $OCH_3$ | H | H | O | |
| 1.61 | Cl | $OCHF_2$ | $OCHF_2$ | $OCH_3$ | H | H | O | |
| 1.62 | Cl | $OCHF_2$ | $OC_2H_4OCH_3$ | $OCH_3$ | H | H | O | |
| 1.63 | Cl | $OCHF_2$ | Cl | $OCH_3$ | H | H | O | |
| 1.64 | Cl | $OCHF_2$ | $OC_2H_5$ | $OCH_3$ | H | H | O | |
| 1.65 | $CH_3$ | $CF_3$ | $OCH_3$ | $CH_3$ | H | H | O | |
| 1.66 | $CH_3$ | $CF_3$ | $OCH_3$ | $C_2H_5$ | H | H | O | |
| 1.67 | $CH_3$ | $CF_3$ | $OCH_3$ | $SCH_3$ | H | H | O | |
| 1.68 | $CH_3$ | $CF_3$ | $OCH_3$ | $OC_2H_5$ | H | H | O | |
| 1.69 | $CH_3$ | $CF_3$ | $OCH_3$ | $N(CH_3)_2$ | H | H | O | |
| 1.70 | $CH_3$ | $CF_3$ | $CH_3$ | $OC_2H_5$ | H | H | O | |
| 1.71 | $CH_3$ | $CF_3$ | $OCH_2CH_3$ | $OC_2H_5$ | H | H | O | |
| 1.72 | $CH_3$ | $CF_3$ | $CH_3$ | $CH_3$ | H | H | O | |
| 1.73 | Cl | $CF_3$ | $OCH_3$ | $CH_3$ | H | H | O | |
| 1.74 | Cl | $CF_3$ | $OCH_3$ | $C_2H_5$ | H | H | O | |
| 1.75 | Cl | $CF_3$ | $OCH_3$ | $SCH_3$ | H | H | O | |
| 1.76 | Cl | $CF_3$ | $OCH_3$ | $OC_2H_5$ | H | H | O | |
| 1.77 | Cl | $CF_3$ | $OCH_3$ | $N(CH_3)_2$ | H | H | O | |
| 1.78 | Cl | $CF_3$ | $CH_3$ | $OC_2H_5$ | H | H | O | |
| 1.79 | Cl | $CF_3$ | $OCH_2CH_3$ | $OC_2H_5$ | H | H | O | |
| 1.80 | Cl | $CF_3$ | $OCH_3$ | $OCH_2CF_3$ | H | H | O | |
| 1.81 | Cl | $CF_3$ | $CH_3$ | $CH_3$ | H | H | O | |
| 1.82 | $CH_3$ | $NO_2$ | $OCH_3$ | $CH_3$ | H | H | O | |
| 1.83 | $CH_3$ | $NO_2$ | $OCH_3$ | $C_2H_5$ | H | H | O | |
| 1.84 | $CH_3$ | $NO_2$ | $OCH_3$ | $SCH_3$ | H | H | O | |
| 1.85 | $CH_3$ | $NO_2$ | $OCH_3$ | $OC_2H_5$ | H | H | O | |
| 1.86 | $CH_3$ | $NO_2$ | $OCH_3$ | $N(CH_3)_2$ | H | H | O | |
| 1.87 | $CH_3$ | $NO_2$ | $CH_3$ | $OC_2H_5$ | H | H | O | |
| 1.88 | $CH_3$ | $NO_2$ | $OCH_2CH_3$ | $OC_2H_5$ | H | H | O | |
| 1.89 | $CH_3$ | $NO_2$ | $CH_3$ | $CH_3$ | H | H | O | |
| 1.90 | $CH_3$ | $NO_2$ | $OCH_3$ | $OCH_2CF_3$ | H | H | O | |
| 1.91 | Cl | $NO_2$ | $OCH_3$ | $CH_3$ | H | H | O | |
| 1.92 | Cl | $NO_2$ | $OCH_3$ | $C_2H_5$ | H | H | O | |
| 1.93 | Cl | $NO_2$ | $OCH_3$ | $SCH_3$ | H | H | O | |
| 1.94 | Cl | $NO_2$ | $OCH_3$ | $OC_2H_5$ | H | H | O | |
| 1.95 | Cl | $NO_2$ | $OCH_3$ | $N(CH_3)_2$ | H | H | O | |
| 1.96 | Cl | $NO_2$ | $CH_3$ | $OC_2H_5$ | H | H | O | |
| 1.97 | Cl | $NO_2$ | $OCH_2CH_3$ | $OC_2H_5$ | H | H | O | |
| 1.98 | Cl | $NO_2$ | $OCH_3$ | $OCH_2CF_3$ | H | H | O | |
| 1.99 | Cl | $NO_2$ | $CH_3$ | $CH_3$ | H | H | O | |
| 1.100 | $CH_3$ | $OCHF_2$ | $OCH_3$ | $CH_3$ | H | H | O | |
| 1.101 | $CH_3$ | $OCHF_2$ | $OCH_3$ | $C_2H_5$ | H | H | O | |
| 1.102 | $CH_3$ | $OCHF_2$ | $OCH_3$ | $SCH_3$ | H | H | O | |
| 1.103 | $CH_3$ | $OCHF_2$ | $OCH_3$ | $OC_2H_5$ | H | H | O | |
| 1.104 | $CH_3$ | $OCHF_2$ | $OCH_3$ | $N(CH_3)_2$ | H | H | O | |
| 1.105 | $CH_3$ | $OCHF_2$ | $CH_3$ | $OC_2H_5$ | H | H | O | |
| 1.106 | $CH_3$ | $OCHF_2$ | $OCH_2CH_3$ | $OC_2H_5$ | H | H | O | |
| 1.107 | $CH_3$ | $OCHF_2$ | $CH_3$ | $CH_3$ | H | H | O | |
| 1.108 | $CH_3$ | $OCHF_2$ | $OCH_3$ | $OCH_2CF_3$ | H | H | O | |
| 1.109 | $CH_3$ | $COOCH_3$ | $OCH_3$ | $CH_3$ | H | H | O | |
| 1.110 | $CH_3$ | $COOCH_3$ | $OCH_3$ | $C_2H_5$ | H | H | O | 182–183° |
| 1.111 | $CH_3$ | $COOCH_3$ | $OCH_3$ | $OC_2H_5$ | H | H | O | |
| 1.112 | $CH_3$ | $COOCH_3$ | $OCH_3$ | $N(CH_3)_2$ | H | H | O | |
| 1.113 | $CH_3$ | $COOCH_3$ | $CH_3$ | $OC_2H_5$ | H | H | O | |
| 1.114 | $CH_3$ | $COOCH_3$ | $OCH_2CH_3$ | $OC_2H_5$ | H | H | O | |
| 1.115 | $CH_3$ | $COOCH_3$ | $OCH_3$ | $OCH_2CF_3$ | H | H | O | |
| 1.116 | $CH_3$ | $COOCH_3$ | $CH_3$ | $CH_3$ | H | H | O | |
| 1.117 | $CH_3$ | $COOCH_3$ | Cl | $C_2H_5$ | H | H | O | 199–200° |
| 1.118 | Cl | $OCHF_2$ | $OCH_3$ | $CH_3$ | H | H | O | 212–213° |
| 1.119 | Cl | $OCHF_2$ | $OCH_3$ | $C_2H_5$ | H | H | O | |
| 1.120 | Cl | $OCHF_2$ | $OCH_3$ | $SCH_3$ | H | H | O | |
| 1.121 | Cl | $OCHF_2$ | $OCH_3$ | $OC_2H_5$ | H | H | O | |
| 1.122 | Cl | $OCHF_2$ | $OCH_3$ | $N(CH_3)_2$ | H | H | O | 218–219° |
| 1.123 | Cl | $OCHF_2$ | $CH_3$ | $OC_2H_5$ | H | H | O | |
| 1.124 | Cl | $OCHF_2$ | $OCH_2CH_3$ | $OC_2H_5$ | H | H | O | |
| 1.125 | Cl | $OCHF_2$ | $CH_3$ | $CH_3$ | H | H | O | |
| 1.126 | Cl | $OCHF_2$ | $OCH_3$ | $OCH_2CF_3$ | H | H | O | |
| 1.127 | Cl | $COOCH_3$ | $OCH_3$ | $CH_3$ | H | H | O | |
| 1.128 | Cl | $COOCH_3$ | $OCH_3$ | $C_2H_5$ | H | H | O | |

TABLE 1-continued

| No. | Q | $R_1$ | $R_2$ | $R_3$ | $R_4$ | $R_5$ | Z | Phys. data m.p. °C. |
|---|---|---|---|---|---|---|---|---|
| 1.129 | Cl | COOCH$_3$ | OCH$_3$ | SCH$_3$ | H | H | O | |
| 1.130 | Cl | COOCH$_3$ | OCH$_3$ | N(CH$_3$)$_2$ | H | H | O | |
| 1.131 | Cl | COOCH$_3$ | CH$_3$ | OC$_2$H$_5$ | H | H | O | |
| 1.132 | Cl | COOCH$_3$ | OCH$_2$CH$_3$ | OC$_2$H$_5$ | H | H | O | |
| 1.133 | Cl | COOCH$_3$ | OCH$_3$ | OC$_2$H$_5$ | H | H | O | |
| 1.134 | Cl | COOCH$_3$ | CH$_3$ | CH$_3$ | H | H | O | 174–175° |
| 1.135 | Cl | COOCH$_3$ | OCH$_3$ | Cl | H | H | O | 215–218° |
| 1.136 | F | COOCH$_3$ | CH$_3$ | OCH$_3$ | H | H | O | |
| 1.137 | F | COOCH$_3$ | OCH$_3$ | OCH$_3$ | H | H | O | 181–182° |
| 1.138 | F | COOCH$_3$ | N(CH$_3$)$_2$ | OCH$_3$ | H | H | O | |
| 1.139 | F | COOCH$_3$ | C$_2$H$_5$ | OCH$_3$ | H | H | O | |
| 1.140 | NO$_2$ | COOCH$_3$ | CH$_3$ | OCH$_3$ | H | H | O | |
| 1.141 | NO$_2$ | COOCH$_3$ | OCH$_3$ | OCH$_3$ | H | H | O | |
| 1.142 | NO$_2$ | COOCH$_3$ | N(CH$_3$)$_2$ | OCH$_3$ | H | H | O | |
| 1.143 | NO$_2$ | COOCH$_3$ | C$_2$H$_5$ | OCH$_3$ | H | H | O | |
| 1.144 | NH$_2$ | COOCH$_3$ | CH$_3$ | OCH$_3$ | H | H | O | |
| 1.145 | NH$_2$ | COOCH$_3$ | OCH$_3$ | OCH$_3$ | H | H | O | |
| 1.146 | NH$_2$ | COOCH$_3$ | N(CH$_3$)$_2$ | OCH$_3$ | H | H | O | |
| 1.147 | NH$_2$ | COOCH$_3$ | C$_2$H$_5$ | OCH$_3$ | H | H | O | |
| 1.148 | CF$_3$ | COOCH$_3$ | CH$_3$ | OCH$_3$ | H | H | O | |
| 1.149 | CF$_3$ | COOCH$_3$ | OCH$_3$ | OCH$_3$ | H | H | O | |
| 1.150 | CF$_3$ | COOCH$_3$ | N(CH$_3$)$_2$ | OCH$_3$ | H | H | O | |
| 1.151 | CF$_3$ | COOCH$_3$ | C$_2$H$_5$ | OCH$_3$ | H | H | O | |
| 1.152 | CF$_3$ | COOCH$_3$ | F | N(CH$_3$)$_2$ | H | H | O | 157–158° |
| 1.153 | CF$_3$ | COOCH$_3$ | F | NHCH$_3$ | H | H | O | 135–137° |
| 1.154 | C$_2$H$_5$ | COOCH$_3$ | CH$_3$ | OCH$_3$ | H | H | O | |
| 1.155 | C$_2$H$_5$ | COOCH$_3$ | OCH$_3$ | OCH$_3$ | H | H | O | |
| 1.156 | C$_2$H$_5$ | COOCH$_3$ | N(CH$_3$)$_2$ | OCH$_3$ | H | H | O | |
| 1.157 | C$_2$H$_5$ | COOCH$_3$ | C$_2$H$_5$ | OCH$_3$ | H | H | O | |
| 1.158 | OCH$_3$ | COOCH$_3$ | CH$_3$ | OCH$_3$ | H | H | O | |
| 1.159 | OCH$_3$ | COOCH$_3$ | OCH$_3$ | OCH$_3$ | H | H | O | |
| 1.160 | OCH$_3$ | COOCH$_3$ | N(CH$_3$)$_2$ | OCH$_3$ | H | H | O | |
| 1.161 | OCH$_3$ | COOCH$_3$ | C$_2$H$_5$ | OCH$_3$ | H | H | O | |
| 1.162 | CHO | COOCH$_3$ | CH$_3$ | OCH$_3$ | H | H | O | |
| 1.163 | CHO | COOCH$_3$ | OCH$_3$ | OCH$_3$ | H | H | O | 184–185° |
| 1.164 | CHO | COOCH$_3$ | N(CH$_3$)$_2$ | OCH$_3$ | H | H | O | |
| 1.165 | CHO | COOCH$_3$ | C$_2$H$_5$ | OCH$_3$ | H | H | O | |
| 1.166 | COOCH$_3$ | COOCH$_3$ | CH$_3$ | OCH$_3$ | H | H | O | |
| 1.167 | COOCH$_3$ | COOCH$_3$ | OCH$_3$ | OCH$_3$ | H | H | O | |
| 1.168 | COOCH$_3$ | COOCH$_3$ | N(CH$_3$)$_2$ | OCH$_3$ | H | H | O | |
| 1.169 | COOCH$_3$ | COOCH$_3$ | C$_2$H$_5$ | OCH$_3$ | H | H | O | |
| 1.170 | CH$_3$ | NO$_2$ | CH$_3$ | OCH$_3$ | H | H | O | |
| 1.171 | CH$_3$ | NO$_2$ | OCH$_3$ | OCH$_3$ | H | H | O | 202–203° |
| 1.172 | CH$_3$ | NO$_2$ | N(CH$_3$)$_2$ | OCH$_3$ | H | H | O | |
| 1.173 | CH$_3$ | NO$_2$ | C$_2$H$_5$ | OCH$_3$ | H | H | O | |
| 1.174 | Cl | NO$_2$ | CH$_3$ | OCH$_3$ | H | H | O | |
| 1.175 | Cl | NO$_2$ | OCH$_3$ | OCH$_3$ | H | H | O | |
| 1.176 | Cl | NO$_2$ | N(CH$_3$)$_2$ | OCH$_3$ | H | H | O | 185–186° |
| 1.177 | Cl | NO$_2$ | C$_2$H$_5$ | OCH$_3$ | H | H | O | |
| 1.178 | CH$_3$ | CF$_3$ | CH$_3$ | OCH$_3$ | H | H | O | |
| 1.179 | CH$_3$ | CF$_3$ | OCH$_3$ | OCH$_3$ | H | H | O | |
| 1.180 | CH$_3$ | CF$_3$ | N(CH$_3$)$_2$ | OCH$_3$ | H | H | O | |
| 1.181 | CH$_3$ | CF$_3$ | C$_2$H$_5$ | OCH$_3$ | H | H | O | |
| 1.182 | Cl | CF$_3$ | CH$_3$ | OCH$_3$ | H | H | O | |
| 1.183 | Cl | CF$_3$ | OCH$_3$ | OCH$_3$ | H | H | O | |
| 1.184 | Cl | CF$_2$ | N(CH$_3$)$_2$ | OCH$_3$ | H | H | O | |
| 1.185 | CL | CF$_3$ | C$_2$H$_5$ | OCH$_3$ | H | H | O | |
| 1.186 | SCH$_3$ | COOCH$_3$ | CH$_3$ | OCH$_3$ | H | H | O | |
| 1.187 | SCH$_3$ | COOCH$_3$ | OCH$_3$ | OCH$_3$ | H | H | O | |
| 1.188 | SCH$_3$ | COOCH$_3$ | N(CH$_3$)$_2$ | OCH$_3$ | H | H | O | |
| 1.189 | SCH$_3$ | COOCH$_3$ | C$_2$H$_5$ | OCH$_3$ | H | H | O | |
| 1.190 | SOCH$_3$ | COOCH$_3$ | CH$_3$ | OCH$_3$ | H | H | O | |
| 1.191 | SOCH$_3$ | COOCH$_3$ | OCH$_3$ | OCH$_3$ | H | H | O | |
| 1.192 | SOCH$_3$ | COOCH$_3$ | N(CH$_3$)$_2$ | OCH$_3$ | H | H | O | |
| 1.193 | SOCH$_3$ | COOCH$_3$ | C$_2$H$_5$ | OCH$_3$ | H | H | O | |
| 1.194 | SO$_2$CH$_3$ | COOCH$_3$ | CH$_3$ | OCH$_3$ | H | H | O | |
| 1.195 | SO$_2$CH$_3$ | COOCH$_3$ | OCH$_3$ | OCH$_3$ | H | H | O | |
| 1.196 | SO$_2$CH$_3$ | COOCH$_3$ | N(CH$_3$)$_2$ | OCH$_3$ | H | H | O | |
| 1.197 | SO$_2$CH$_3$ | COOCH$_3$ | C$_2$H$_5$ | OCH$_3$ | H | H | O | |
| 1.198 | CN | COOCH$_3$ | CH$_3$ | OCH$_3$ | H | H | O | |
| 1.199 | CN | COOCH$_3$ | OCH$_3$ | OCH$_3$ | H | H | O | |
| 1.200 | CN | COOCH$_3$ | N(CH$_3$)$_2$ | OCH$_3$ | H | H | O | |
| 1.201 | CN | COOCH$_3$ | C$_2$H$_5$ | OCH$_3$ | H | H | O | |
| 1.202 | CH$_3$ | COSCH$_3$ | OCH$_3$ | OCH$_3$ | H | H | O | |
| 1.203 | CH$_3$ | CH$_2$OCH$_3$ | OCH$_3$ | OCH$_3$ | H | H | O | |
| 1.204 | CH$_3$ | CH$_2$SCH$_3$ | OCH$_3$ | OCH$_3$ | H | H | O | |
| 1.205 | CH$_3$ | CH$_2$SOCH$_3$ | OCH$_3$ | OCH$_3$ | H | H | O | |
| 1.206 | CH$_3$ | CH$_2$SO$_2$CH$_3$ | OCH$_3$ | OCH$_3$ | H | H | O | |
| 1.207 | CH$_3$ | C$_2$H$_4$OCH$_3$ | OCH$_3$ | OCH$_3$ | H | H | O | |
| 1.208 | CH$_3$ | SCH$_2$CH=CH$_2$ | OCH$_3$ | OCH$_3$ | H | H | O | |

TABLE 1-continued

| No. | Q | R$_1$ | R$_2$ | R$_3$ | R$_4$ | R$_5$ | Z | Phys. data m.p. °C. |
|---|---|---|---|---|---|---|---|---|
| 1.209 | CH$_3$ | OCH$_2$CCl=CH$_2$ | OCH$_3$ | OCH$_3$ | H | H | O | |
| 1.210 | CH$_3$ | CH=CHCN | OCH$_3$ | OCH$_3$ | H | H | O | |
| 1.211 | CH$_3$ | C$_3$H$_6$OCH$_3$ | OCH$_3$ | OCH$_3$ | H | H | O | |
| 1.212 | CH$_3$ | CH$_2$COCH$_3$ | OCH$_3$ | OCH$_3$ | H | H | O | |
| 1.213 | CH$_3$ | OCH$_3$ | OCH$_3$ | OCH$_3$ | H | H | O | |
| 1.214 | CH$_3$ | OC$_2$H$_5$ | OCH$_3$ | OCH$_3$ | H | H | O | 216–217° |
| 1.215 | CH$_3$ | OC$_2$H$_4$OCH$_3$ | OCH$_3$ | OCH$_3$ | H | H | O | |
| 1.216 | CH$_3$ | OCH$_2$CH=CH$_2$ | OCH$_3$ | OCH$_3$ | H | H | O | |
| 1.217 | CH$_3$ | OCH$_2$CH≡CH | OCH$_3$ | OCH$_3$ | H | H | O | |
| 1.218 | CH$_3$ | OCF$_3$ | OCH$_3$ | OCH$_3$ | H | H | O | 189–190° |
| 1.219 | CH$_3$ | OCF$_2$CHF$_2$ | OCH$_3$ | OCH$_3$ | H | H | O | |
| 1.220 | CH$_3$ | OCF$_2$CF$_3$ | OCH$_3$ | OCH$_3$ | H | H | O | |
| 1.221 | CH$_3$ | OCH$_2$CH$_2$Cl | OCH$_3$ | OCH$_3$ | H | H | O | 214–215° |
| 1.222 | CH$_3$ | OCHCl=CHCl | OCH$_3$ | OCH$_3$ | H | H | O | 222–223° |
| 1.223 | CH$_3$ | CH$_3$ | OCH$_3$ | OCH$_3$ | H | H | O | |
| 1.224 | CH$_3$ | C$_2$H$_5$ | OCH$_3$ | OCH$_3$ | H | H | O | |
| 1.225 | CH$_3$ | nC$_3$H$_7$ | OCH$_3$ | OCH$_3$ | H | H | O | |
| 1.226 | CH$_3$ | SCF$_3$ | OCH$_3$ | OCH$_3$ | H | H | O | |
| 1.227 | CH$_3$ | CH$_2$Cl | OCH$_3$ | OCH$_3$ | H | H | O | |
| 1.228 | CH$_3$ | C$_2$H$_4$CF$_3$ | OCH$_3$ | OCH$_3$ | H | H | O | |
| 1.229 | CH$_3$ | Br | OCH$_3$ | OCH$_3$ | H | H | O | |
| 1.230 | CH$_3$ | F | OCH$_3$ | OCH$_3$ | H | H | O | |
| 1.231 | CH$_3$ | SCH$_3$ | OCH$_3$ | OCH$_3$ | H | H | O | |
| 1.232 | CH$_3$ | SOCH$_3$ | OCH$_3$ | OCH$_3$ | H | H | O | |
| 1.233 | CH$_3$ | SO$_2$CH$_3$ | OCH$_3$ | OCH$_3$ | H | H | O | |
| 1.234 | CH$_3$ | SO$_2$C$_3$H$_7$n | OCH$_3$ | OCH$_3$ | H | H | O | |
| 1.235 | CH$_3$ | SO$_2$N(CH$_3$)$_2$ | OCH$_3$ | OCH$_3$ | H | H | O | |
| 1.236 | CH$_3$ | CHO | OCH$_3$ | OCH$_3$ | H | H | O | |
| 1.237 | CH$_3$ | COCH$_3$ | OCH$_3$ | OCH$_3$ | H | H | O | |
| 1.238 | CH$_3$ | COOC$_2$H$_5$ | OCH$_3$ | OCH$_3$ | H | H | O | |
| 1.239 | CH$_3$ | COOCH$_2$CH=CH$_2$ | OCH$_3$ | OCH$_3$ | H | H | O | |
| 1.240 | CH$_3$ | OSO$_2$CH$_3$ | OCH$_3$ | OCH$_3$ | H | H | O | |
| 1.241 | CH$_3$ | OSO$_2$CF$_3$ | OCH$_3$ | OCH$_3$ | H | H | O | |
| 1.242 | CH$_3$ | COCF$_3$ | OCH$_3$ | OCH$_3$ | H | H | O | |
| 1.243 | CH$_3$ | CH=CH$_2$ | OCH$_3$ | OCH$_3$ | H | H | O | |
| 1.244 | CH$_3$ | CH=CHCH$_3$ | OCH$_3$ | OCH$_3$ | H | H | O | |
| 1.245 | CH$_3$ | CH=CCl$_2$ | OCH$_3$ | OCH$_3$ | H | H | O | |
| 1.246 | CH$_3$ | CH=CHCF$_3$ | OCH$_3$ | OCH$_3$ | H | H | O | |
| 1.247 | CH$_3$ | CH$_2$CN | OCH$_3$ | OCH$_3$ | H | H | O | |
| 1.248 | CH$_3$ | CON(CH$_3$)$_2$ | OCH$_3$ | OCH$_3$ | H | H | O | |
| 1.249 | Cl | OCH$_3$ | OCH$_3$ | OCH$_3$ | 5-OCH$_3$ | H | O | 201–203° |
| 1.250 | SOCH$_3$ | Cl | OCH$_3$ | OCH$_3$ | H | H | O | 161–165° |
| 1.251 | NO$_2$ | Cl | Cl | C$_2$H$_5$ | H | H | O | 119° |
| 1.252 | CN | Cl | CH$_3$ | H | H | H | O | 159–161° |
| 1.253 | CN | Cl | CH$_3$ | Cl | H | H | O | 143–144° |
| 1.254 | NO$_2$ | Cl | CH$_3$ | OCH$_3$ | H | H | O | 154–155° |
| 1.255 | NO$_2$ | Cl | Cl | SCH$_3$ | H | H | O | 75–80° |
| 1.256 | NO$_2$ | Cl | NH$_2$ | SCH$_3$ | H | H | O | 218–220° |
| 1.257 | NO$_2$ | Cl | Cl | CH$_3$ | H | H | O | 121–124° |
| 1.258 | NO$_2$ | Cl | OCH$_3$ | CH$_3$ | H | H | O | 190–192° |
| 1.259 | Cl | SCHF$_2$ | OCH$_3$ | OCH$_3$ | H | H | O | 184–185° |
| 1.260 | F | OCHF$_2$ | OCH$_3$ | OCH$_3$ | H | H | O | 156–157° |
| 1.261 | F | Cl | OCH$_3$ | OCH$_3$ | H | H | O | 216–217° |
| 1.262 | Br | COOCH$_3$ | CH$_3$ | OCH$_3$ | H | H | O | 177–178° |
| 1.263 | NH$_2$ | Cl | CH$_3$ | OCH$_3$ | H | H | O | 175–178° decomp. |
| 1.264 | CH$_3$ | COOCH$_3$ | OCH$_3$ | OCH$_3$ | H | CH$_3$ | O | |
| 1.265 | CH$_3$ | COOCH$_3$ | OCH$_3$ | OCH$_3$ | H | H | S | |
| 1.266 | CH$_3$ | Cl | OCH$_3$ | OCH$_3$ | H | H | S | |
| 1.267 | CH$_3$ | OCHF$_2$ | OCH$_3$ | OCH$_3$ | H | H | S | |
| 1.268 | CH$_3$ | OCHF$_2$ | OCH$_3$ | OCH$_3$ | H | CH$_3$ | O | |
| 1.269 | CH$_3$ | COOCH$_3$ | CH$_3$ | OCH$_3$ | H | CH$_3$ | O | |
| 1.270 | Cl | OC$_2$H$_2$OCH$_3$ | N(CH$_3$)$_2$ | OCH$_3$ | H | H | O | 165–166° |
| 1.271 | NO$_2$ | OCHF$_2$ | CH$_3$ | OCH$_3$ | H | H | O | 145–146° |
| 1.272 | CH$_3$ | Cl | OCH$_3$ | OCH$_3$ | H | H | O | 221–222° |
| 1.273 | F | COOCH$_3$ | H | OCH$_3$ | H | H | O | 196–197° |
| 1.274 | Cl | COOCH$_3$ | H | OCH$_3$ | H | H | O | 190–192° |
| 1.275 | CH$_2$CH$_3$ | COOCH$_3$ | OCHF$_2$ | C$_3$H$_7$(n) | H | H | O | 170–171° |
| 1.276 | SO$_2$CH$_3$ | COOCH$_3$ | OCH$_3$ | NHC$_3$H$_7$(i) | H | H | O | 231–233° |
| 1.277 | SO$_2$CH$_3$ | COOCH$_3$ | NHC$_3$H$_7$(i) | OCH$_3$ | H | H | O | 181–183° |
| 1.278 | CH$_3$ | COOCH$_3$ | OCH$_3$ | CH$_2$OCH$_3$ | H | H | O | 170–171° |
| 1.279 | C$_3$H$_7$(i) | COOCH$_3$ | OCH$_3$ | OCH$_3$ | H | H | O | 170–171° |
| 1.280 | CH$_3$ | COOCH$_3$ | Cl | CH$_2$OCH$_3$ | H | H | O | 193–194° |
| 1.281 | CH$_3$ | COOCH$_3$ | OCH$_2$CH$_3$ | CH$_2$OCH$_3$ | H | H | O | 163–164° |
| 1.282 | SCH$_3$ | COOCH$_3$ | OCH$_3$ | C$_3$H$_7$(i) | H | H | O | 146–147° |
| 1.283 | SOCH$_3$ | COOCH$_3$ | OCH$_3$ | C$_3$H$_7$(i) | H | H | O | 167–168° |
| 1.284 | SO$_2$CH$_3$ | COOCH$_3$ | OCH$_3$ | C$_3$H$_7$(i) | H | H | O | 152–153° |
| 1.285 | J | COOCH$_3$ | OCH$_3$ | OCH$_3$ | H | H | O | 175–176° |
| 1.286 | —CH=CH$_2$ | COOCH$_3$ | OCH$_3$ | OCH$_3$ | H | H | O | 144–145° |
| 1.287 | —C≡CH | COOCH$_3$ | OCH$_3$ | OCH$_3$ | H | H | O | 146–149° |

TABLE 1-continued

| No. | Q | R₁ | R₂ | R₃ | R₄ | R₅ | Z | Phys. data m.p. °C. |
|---|---|---|---|---|---|---|---|---|
| | | | | | | | | decomp. |
| 1.288 | Cl | OCH₂CH₂Cl | OCH₃ | OCH₃ | H | H | O | |
| 1.289 | Cl | OC₂H₂OCH₃ | OCH₃ | OCH₃ | H | H | O | |
| 1.290 | Cl | OCH₃ | OCH₃ | OCH₃ | H | H | O | |
| 1.291 | Cl | OCH₂CH₃ | OCH₃ | OCH₃ | H | H | O | |
| 1.292 | Cl | OCCl=CHCl | OCH₃ | OCH₃ | H | H | O | |
| 1.293 | Cl | SCH₂CH₂Cl | OCH₃ | OCH₃ | H | H | O | |
| 1.294 | Cl | OCF₂CHF₂ | OCH₃ | OCH₃ | H | H | O | |
| 1.295 | Cl | OCF₂CF₃ | OCH₃ | OCH₃ | H | H | O | |
| 1.296 | Cl | Cl | OCH₃ | OCH₃ | H | H | O | |
| 1.297 | Cl | F | OCH₃ | OCH₃ | H | H | O | |
| 1.298 | Cl | CH=CH—CF₃ | OCH₃ | OCH₃ | H | H | O | |
| 1.299 | Cl | SO₂N(CH₃)₂ | OCH₃ | OCH₃ | H | H | O | |
| 1.300 | Cl | CON(CH₃)₂ | OCH₃ | OCH₃ | H | H | O | |
| 1.301 | F | OCH₂CH₂Cl | OCH₃ | OCH₃ | H | H | O | |
| 1.302 | F | OC₂H₄OCH₃ | OCH₃ | OCH₃ | H | H | O | |
| 1.303 | F | OCH₃ | OCH₃ | OCH₃ | H | H | O | |
| 1.304 | F | OCH₂CH₃ | OCH₃ | OCH₃ | H | H | O | |
| 1.305 | F | OCCl=CHCl | OCH₃ | OCH₃ | H | H | O | |
| 1.306 | F | NO₂ | OCH₃ | OCH₃ | H | H | O | |
| 1.307 | F | OCH₂—CH=CH₂ | OCH₃ | OCH₃ | H | H | O | |
| 1.308 | Cl | OCH₂—CH=CH₂ | OCH₃ | OCH₃ | H | H | O | |
| 1.309 | Cl | OCH₂CF₃ | OCH₃ | OCH₃ | H | H | O | |
| 1.310 | Cl | OCH₂CH₂Cl | CH₃ | OCH₃ | H | H | O | |
| 1.311 | Cl | OC₂H₄OCH₃ | CH₃ | OCH₃ | H | H | O | |
| 1.312 | Cl | OCH₃ | CH₃ | OCH₃ | H | H | O | |
| 1.313 | Cl | OCH₂CH₃ | CH₃ | OCH₃ | H | H | O | |
| 1.314 | Cl | OCCl=CHCl | CH₃ | OCH₃ | H | H | O | |
| 1.315 | Cl | OCH₂—CH=CH₂ | CH₃ | OCH₃ | H | H | O | |
| 1.316 | Cl | Cl | CH₃ | OCH₃ | H | H | O | |
| 1.317 | Cl | F | CH₃ | OCH₃ | H | H | O | |
| 1.318 | Cl | SCHF₂ | CH₃ | OCH₃ | H | H | O | |
| 1.319 | NO₂ | F | CH₃ | OCH₃ | H | H | O | |
| 1.320 | NO₂ | SCHF₂ | CH₃ | OCH₃ | H | H | O | |
| 1.321 | NO₂ | OCH₂OCH₂Cl | CH₃ | OCH₃ | H | H | O | |
| 1.322 | NO₂ | OCCl=CHCl | CH₃ | OCH₃ | H | H | O | |
| 1.323 | NO₂ | OC₂H₄OCH₃ | CH₃ | OCH₃ | H | H | O | |
| 1.324 | NO₂ | OCH₂CH=CH₂ | CH₃ | OCH₃ | H | H | O | |
| 1.325 | NO₂ | Cl | OCH₃ | OCH₃ | H | H | O | |
| 1.326 | NO₂ | F | OCH₃ | OCH₃ | H | H | O | |
| 1.327 | NO₂ | OCHF₂ | OCH₃ | OCH₃ | H | H | O | |
| 1.328 | NO₂ | SCHF₂ | OCH₃ | OCH₃ | H | H | O | |
| 1.329 | NO₂ | OCH₂CH₂Cl | OCH₃ | OCH₃ | H | H | O | |
| 1.330 | NO₂ | OCCl=CHCl | OCH₃ | OCH₃ | H | H | O | |
| 1.331 | NO₂ | OC₂H₄OCH₃ | OCH₃ | OCH₃ | H | H | O | |
| 1.332 | NO₂ | OCH₂CH=CH₂ | OCH₃ | OCH₃ | H | H | O | |
| 1.333 | NH₂ | OCHF₂ | OCH₃ | OCH₃ | H | H | O | |
| 1.334 | NH₂ | OCHF₂ | CH₃ | OCH₃ | H | H | O | |
| 1.335 | SOCH₃ | NO₂ | OCH₃ | OCH₃ | H | H | O | |
| 1.336 | SOCH₃ | NO₂ | CH₃ | OCH₃ | H | H | O | |
| 1.337 | SOCH₃ | OCHF₂ | OCH₃ | OCH₃ | H | H | O | |
| 1.338 | SOCH₃ | OCHF₂ | CH₃ | OCH₃ | H | H | O | |

TABLE 2

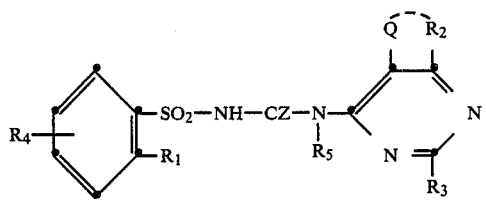

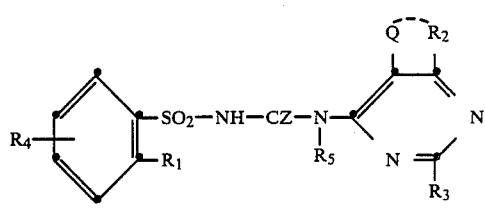

| No. | R₁ | —Q—R₂— | R₃ | R₄ | R₅ | Z |
|---|---|---|---|---|---|---|
| 2.1 | COOCH₃ | —C₃H₆— | OCH₃ | H | H | O |
| 2.2 | COOCH₃ | —C₄H₈— | OCH₃ | H | H | O |
| 2.3 | COOCH₃ | —OC₃H₆— | OCH₃ | H | H | O |
| 2.4 | COOCH₂ | —C₂H₄O— | OCH₃ | H | H | O |

TABLE 3

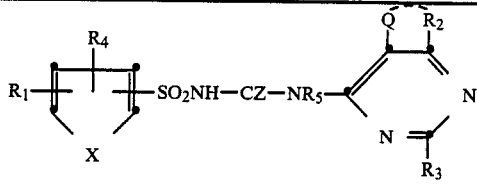

| No. | Q | $R_1$ | $R_2$ | $R_3$ | $R_4$ | $R_5$ | X | Z | Position of the $SO_2$ group |
|---|---|---|---|---|---|---|---|---|---|
| 3.1 | $CH_3$ | 3-$COOCH_3$ | $OCH_3$ | $OCH_3$ | H | H | S | O | 2 |
| 3.2 | $CH_3$ | 2-$COOCH_3$ | $OCH_3$ | $OCH_3$ | H | H | S | O | 3 |
| 3.3 | $CH_3$ | 3-$COOCH_3$ | $OCH_3$ | $OCH_3$ | H | H | S | O | 4 |
| 3.4 | $CH_3$ | H | $OCH_3$ | $OCH_3$ | H | H | NH | O | 2 |
| 3.5 | $CH_3$ | H | $OCH_3$ | $OCH_3$ | H | H | NH | O | 2 |
| 3.6 | $CH_3$ | 2-Cl | $OCH_3$ | $OCH_3$ | H | H | $-CH=N-$ | O | 3 |
| 3.7 | $CH_3$ | 2-Cl | $CH_3$ | $OCH_3$ | H | H | $-CH=N-$ | O | 3 |
| 3.8 | $CH_3$ | 3-$COOCH_3$ | $CH_3$ | $OCH_3$ | H | H | $-CH=N-$ | O | 2 |
| 3.9 | $CH_3$ | 2-$COOCH_3$ | $CH_3$ | $OCH_3$ | H | H | $-CH=N-$ | O | 3 |
| 3.10 | $CH_3$ | 3-$COOCH_3$ | $CH_3$ | $OCH_3$ | H | H | $-CH=N-$ | O | 4 |
| 3.11 | $CH_3$ | 2-$OCH_2CH=CH_2$ | $CH_2$ | $OCH_3$ | H | H | $-CH=N-$ | O | 3 |
| 3.12 | $CH_3$ | 2-$OCH_2CH-CH_2$ | $OCH_3$ | $OCH_3$ | H | H | $-CH=N-$ | O | 3 |
| 3.13 | $CH_3$ | 2-$OCH_2CH_2CH_2$ | $CH_3$ | $OCH_3$ | H | H | $-CH=N-$ | O | 3 |
| 3.14 | $CH_3$ | 2-$OCH_3CH_2CH_3$ | $OCH_3$ | $OCH_3$ | H | H | $-CH=N-$ | O | 3 |
| 3.15 | $CH_3$ | 2-$OCH_3$ | $CH_3$ | $OCh_3$ | H | H | $-CH=N-$ | O | 3 |
| 3.16 | $CH_3$ | 2-$OCH_3$ | $OCH_3$ | $OCH_3$ | H | H | $-CH=N-$ | O | 3 |
| 3.17 | $CH_3$ | 2-$OCH_2CH=CHCH_3$ | $CH_3$ | $OCH_3$ | H | H | $-CH=N-$ | O | 3 |
| 3.18 | $CH_3$ | 2-$OCH_2CH=CHCH_3$ | $OCH_3$ | $OCH_3$ | H | H | $-CH=N-$ | O | 3 |

TABLE 4

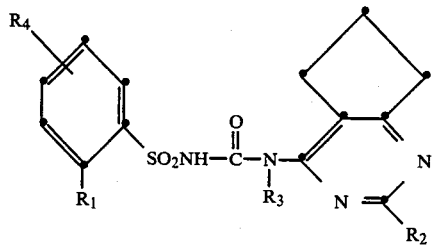

| No. | $R_1$ | $R_2$ | $R_3$ | $R_4$ | Phys. data m.p. °C. |
|---|---|---|---|---|---|
| 4.001 | $COOCH_3$ | $OCH_3$ | H | H | 179–180° decomp. |
| 4.002 | $COOCH_3$ | $OCH_2CF_3$ | H | H | 198–199° |
| 4.003 | $COOCH_3$ | $OCH_2CH_3$ | H | H | 178–180° decomp. |
| 4.004 | $COOCH_3$ | $N(CH_3)_2$ | H | H | |
| 4.005 | $COOCH_3$ | $SCH_3$ | H | H | |
| 4.006 | $COOCH_3$ | Cl | H | H | |
| 4.007 | $COOCH_3$ | $CH_3$ | H | H | 177–178° decomp. |
| 4.008 | $NO_2$ | $OCH_3$ | H | H | |
| 4.009 | $NO_2$ | $OCH_2CF_3$ | H | H | |
| 4.010 | $NO_2$ | Cl | H | H | |
| 4.011 | $NO_2$ | $OCH_2CH_3$ | H | H | |
| 4.012 | Cl | $OCH_3$ | H | H | |
| 4.013 | Cl | $OCH_2CF_3$ | H | H | |
| 4.014 | Cl | $OCH_2CH_3$ | H | H | |
| 4.015 | Cl | Cl | H | H | |
| 4.016 | $OCHF_2$ | $OCH_3$ | H | H | |
| 4.017 | $OCHF_2$ | $OCH_2CF_3$ | H | H | |
| 4.018 | $OCHF_2$ | $OCH_2CH_3$ | H | H | |
| 4.019 | $OCHF_2$ | Cl | H | H | |
| 4.020 | $OCHF_2$ | $CH_3$ | H | H | |

FORMULATION EXAMPLES

EXAMPLE 2

Formulation Examples for active ingredients of the formula I (%=percent by weight)

| (a) Wettable powder | (a) | (b) | (c) |
|---|---|---|---|
| active ingredient | 20% | 60% | 0.5% |
| sodium lignin sulfonate | 5% | 5% | 5% |
| sodium lauryl sulfate | 3% | — | — |
| sodium diisobutylnaphthalene sulfonate | — | 6% | 6% |
| octylphenolpolyethylene glycol ether (7–8 mols of ethylene oxide) | — | 2% | 2% |
| highly dispersed silicic acid | 5% | 27% | 27% |
| kaolin | 67% | — | — |
| sodium chloride | — | — | 59.5% |

The active ingredient is well mixed with the additives and ground in a suitable mill. There are obtained wettable powders which can be diluted with water to give suspensions of the concentration desired.

| (b) Emulsion concentrate | (a) | (b) |
|---|---|---|
| active ingredient | 10% | 1% |
| octylphenolpolyethylene glycol ether (4–5 mols of ethylene oxide) | 3% | 3% |
| calcium dodecyl benzene sulfonate | 3% | 3% |
| castor oil polyglycol ether (36 mols of ethylene oxide) | 4% | 4% |
| cyclohexanone | 30% | 10% |
| xylene mixture | 50% | 79% |

Emulsions of the concentration desired can be obtained from this concentrate by dilution with water.

| (c) Dust | (a) | (b) |
|---|---|---|
| active ingredient | 0.1% | 1% |
| talcum | 99.9% | — |
| kaolin | — | 99% |

Dusts ready for use are obtained by mixing the active-ingredient with the carriers, and grinding the mixture in a suitable mill.

| (d) Extruder granulate | (a) | (b) |
|---|---|---|
| active ingredient | 10% | 1% |
| sodium lignin sulfonate | 2% | 2% |
| carboxymethylcellulose | 1% | 1% |
| kaolin | 87% | 96% |

The active ingredient is mixed with the additives, and the mixture is then ground and moistened with water. It is extruded and subsequently dried in a stream of air.

| (e) Coated granulate | |
|---|---|
| active ingredient | 3% |
| polyethylene glycol (MW 200) | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| active ingredient | 40% | 5% |
| ethylene glycol | 10% | 10% |
| nonylphenolpolyethylene glycol ether (15 mols of ethylene oxide) | 6% | 1% |
| sodium lignin sulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the additives. There is obtained a suspension concentrate from which can be produced, by dilution with water, suspensions of the concentration required.

| (g) Salt solution | |
|---|---|
| active ingredient | 5% |
| isopropylamine | 1% |
| octylphenolpolyethylene glycol ether (78 mols of ethylene oxide) | 3% |
| water | 91% |

EXAMPLE 3

Biological tests

Verification of herbicidal action before emergence of the plants

Plastics pots are filled with expanded vermiculite (density: 0.135 g/cm³, water-absorption capacity: 0.565 l/l). After saturation of the non-adsorptive vermiculite with an aqueous active-ingredient emulsion in deionised water, which contains the active ingredient at a concentration of 70.8 ppm, seeds of the following plants are sown on the surface: Nasturtium officinalis, Agrostis tenuis, Stellaria media and Digitaria sanguinalis. The test vessels are subsequently kept in a climatic chamber at 20° C., with an illumination of about 20 k lux and a relative humidity of 70%. During the germination phase of 4 to 5 days, the pots are covered over with light-permeable material in order to raise the local air humidity and watered with deionised water. After the 5th day, 0.5% of a commercial liquid fertiliser (® Greenzit) is added to the water. The test is evaluated 12 days after sowing, and the effect on the test plants assessed according to the following scale of ratings:

1 plants have not germinated or are totally destroyed
2-3 very strong action
4-6 medium action
7-8 no action (as untreated control plants)

Pre-emergence action

Concentration of the active-ingredient emulsion: 70.8 ppm

| Active ingredient No. | Test plant | | | |
|---|---|---|---|---|
| | Nasturtium officinalis | Stellaria media | Agrostis tenuis | Digitaria sanguinalis |
| 1.002 | 2 | 2 | 2 | 3 |
| 1.012 | 1 | 3 | 1 | 4 |
| 1.017 | 2 | 2 | 3 | 3 |
| 1.018 | 1 | 1 | 3 | 8 |
| 1.020 | 2 | 2 | 2 | 4 |
| 1.031 | 3 | 5 | 3 | 6 |
| 1.034 | 1 | 2 | 1 | 2 |
| 1.049 | 2 | 2 | 2 | 3 |
| 1.052 | 2 | 1 | 1 | 2 |
| 1.110 | 4 | 4 | 7 | 8 |
| 1.122 | 6 | 7 | 7 | 9 |
| 1.125 | 1 | 2 | 1 | 2 |
| 1.134 | 2 | 8 | 2 | 9 |
| 1.135 | 3 | 3 | 6 | 7 |
| 1.137 | 2 | 2 | 1 | 2 |
| 1.152 | 2 | 3 | 2 | 3 |
| 1.155 | 2 | 2 | 2 | 3 |
| 1.171 | 2 | 2 | 3 | 3 |
| 1.176 | 2 | 2 | 2 | 6 |
| 1.191 | 1 | 1 | 1 | 2 |
| 1.195 | 2 | 2 | 2 | 2 |
| 1.214 | 1 | 2 | 1 | 3 |
| 1.218 | 2 | 6 | 2 | 7 |
| 1.221 | 1 | 2 | 2 | 3 |
| 1.222 | 2 | 2 | 2 | 3 |
| 2.261 | 2 | 2 | 2 | 2 |
| 2.262 | 1 | 1 | 2 | 3 |
| 2.270 | 2 | 3 | 2 | 6 |
| 2.271 | 2 | 2 | 2 | 4 |
| 2.272 | 2 | 2 | 4 | 4 |
| 2.273 | 2 | 3 | 2 | 4 |
| 2.274 | 2 | 3 | 4 | 5 |
| 2.277 | 2 | 2 | 4 | 6 |
| 1.277 | 2 | 2 | 4 | 6 |
| 1.278 | 2 | 3 | 4 | 4 |
| 1.279 | 2 | 2 | 2 | 3 |
| 1.280 | 4 | 7 | 5 | 8 |
| 1.282 | 3 | 5 | 4 | 6 |
| 1.285 | 2 | 2 | 3 | 3 |
| 4.002 | 2 | 2 | 2 | 3 |
| 4.003 | 3 | 8 | 3 | 9 |

Verification of the herbicidal action before emergence of the plants

Plant seeds are sown in flower pots (12-15 cm in diameter) in a greenhouse. The surface of the soil is treated immediately afterwards with an aqueous dispersion or solution of the active ingredients, obtained from a flowable or wettable powder. Various concentrations corresponding to specific amounts of active ingredient per hectare are used. The pots are then kept in a greenhouse at a temperature of 22°-25° C. with 50-70% relative humidity. After 3 weeks, the tested compounds of Tables 1-4 exhibit a good action at concentrations of 0.03 to 1 kg per hectare.

Verification of the herbicidal action after emergence of the plants (contact action)

A considerable number of weeds and cultivated plants, both monocotyledonous and dicotyledonous, are sprayed after emergence, in the 4- to 6-left stage, with an aqueous active-ingredient dispersion in varying dosages, and are then kept at 24° to 26° C. with 40–60% relative humidity. The tested compounds of Tables 1–4 exhibit 15 days after the treatment a good herbicidal action.

Verification of the reduction in growth of tropical leguminous cover crops

The test plants (Centrosema plumieri and Centrosema pubescens) are cultivated to the fully grown stage, and then cut back to a height of 60 cm. After 7 days, the active ingredient is sprayed on in the form of an aqueous emulsion. The test plants are maintained at 70% relative humidity and with 6000 lux of artificial light, 14 hours per day, at temperatures of 27° C. by day and 21° C. by night. The test results are assessed 4 weeks after application of the emulsion. The new growth occurring compared with that on the control plants is estimated and weighed, and the phytotoxicity is evaluated. The plants treated with the active ingredients from Tables 1–4 show in this test a clear reduction in new growth (less than 20% of the new growth occurring on untreated control plants), without the test plants having suffered damage.

Verification of reduction in growth of cereals

The cereal varieties Hordeum vulgare (spring barley) and Secale (spring rye) are sown in plastics pots containing sterilised soil in a greenhouse, and watered as required. The young shoots are sprayed, about 21 days after sowing, with the aqueous spray liquor of an active ingredient of the formula I. The amount applied is up to 100 g of active ingredient per hectare, and 21 days after application, the growth of the cereals is assessed. The treated plants show a reduction in the extent of new growth compared with that on the untreated control plants (60–90% of the new growth on the control plants), and also in part an increased in the diameter of the stems of the plants.

Verification of reduction in growth of grasses

The grasses Lolium perenne, Poa pratensis, Festuca ovina, Dactylis glomerata and Cynodon dactylon are sown in a greenhouse, in plastics dishes containing a soil/peat/sand mixture (6:3:1), and watered as required. The emerged grasses are cut back weekly to a height of 4 cm, and are sprayed, about 50 days after sowing and one day after the final cutting, with the aqueous spray liquor of an active ingredient of the formula I. The amount of active ingredient corresponds, when converted, to up to 100 g per hectare. The growth of the grasses is assessed 21 days after application.

The tested compounds of Tables 1–4 effect a reduction of new growth compared with the new growth of the untreated control grasses.

What is claimed is:

1. An N-pyrimidin-4-yl-N'-sulfonylurea of the formula Ia

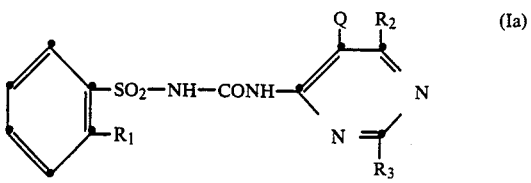

wherein
Q is halogen, $C_1$–$C_4$-alkyl, nitro, amino, formyl, methylthio, methylsulfinyl or methylsulfonyl,
$R_1$ is halogen, nitro, $C_1$–$C_4$-haloalkyl, $C_1$–$C_4$-alkoxy, $C_1$–$C_4$-haloalkoxy, $C_3$–$C_4$-alkenyloxy, $C_2$–$C_4$-haloalkenyloxy, $C_1$–$C_4$-haloalkylthio, $C_1$–$C_4$-alkoxycarbonyl or $C_1$–$C_4$-alkylsulfonyl,
$R_2$ is halogen, $C_1$–$C_3$-alkyl, cyclopropyl, $C_1$–$C_3$-alkoxy, $C_1$–$C_2$-haloalkoxy, amino, methylamino or dimethylamino,
$R_3$ is $C_1$–$C_2$-alkyl, $C_1$–$C_2$-haloalkyl, cyclopropyl, $C_1$–$C_2$-alkoxy, $C_1$–$C_2$-haloalkoxy or difluoromethoxy.

2. An N-pyrimidin-4-yl-N'-sulfonylurea according to claim 1 wherein
$R_1$ is halogen, nitro, $C_1$–$C_4$-haloalkyl, $C_1$–$C_4$-alkoxy, $C_1$–$C_4$-haloalkoxy, $C_1$–$C_4$-haloalkylthio, $C_1$–$C_4$-alkoxycarbonyl or dimethylsulfamoyl,
$R_2$ is halogen, $C_1$–$C_2$-alkyl, $C_1$–$C_2$-alkoxy, $C_1$–$C_2$-haloalkoxy, methylamino or dimethylamino, and
$R_3$ is $C_1$–$C_2$-alkoxy, trifluoroethoxy or difluoromethoxy.

3. N-(2-Methoxycarbonylphenylsulfonyl)-N'-(2,6-dimethoxy-5-methylpyrimidin-4-yl)-urea according to claim 1.

4. N-(2-Difluoromethoxyphenylsulfonyl)-N'-(2,6-dimethoxy-5-methylpyrimidin-4-yl)-urea according to claim 1.

5. A herbicidal and plant-growth regulating or inhibiting composition which contains, as active ingredient, an N-pyrimidin-4-yl-N'-sulfonylurea according to claim 1, together with an inert carrier and/or other additives.

6. A method of controlling undesirable plant growth, which method comprises applying to the plants or to the locus thereof a growth-regulating effective amount of an N-pyrimidin-4-yl-N'-sulfonylurea of claim 1, or of a composition containing it as active ingredient.

7. A method of reducing plant growth, which method comprises applying to the plants or to the locus thereof a growth-regulating effective amount of an N-pyrimidin-4-yl-N'-sulfonylurea of claim 1, or of a composition containing it as active ingredient.

8. A method for the selective, pre- or post-emergence controlling of weeds in crops of cultivated plants, which method comprises applying thereto or to the locus thereof a herbicidally effective amount of an N-pyrimidin-4-yl-N'-sulfonylurea of claim 1, of of a composition containing it as active ingredient.

* * * * *